United States Patent [19]
Connors

[11] Patent Number: 5,824,540
[45] Date of Patent: *Oct. 20, 1998

[54] PSEUDOMONAS PUTIDA STRAIN WITH DIOXYGENASE ACTIVITY

[75] Inventor: Neal C. Connors, Fanwood, N.J.

[73] Assignee: Merck & Co., Inc., Rahway, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 665,660

[22] Filed: Jun. 18, 1996

Related U.S. Application Data

[60] Provisional application No. 60/000,360 Jun. 20, 1995.
[51] Int. Cl.$^6$ ..................................................... C12N 1/20
[52] U.S. Cl. ......................................... 435/253.3; 435/877
[58] Field of Search ................................. 435/253.3, 877

[56] References Cited

U.S. PATENT DOCUMENTS

| | | | |
|---|---|---|---|
| Re. 33,307 | 8/1990 | Taylor et al. ........................... | 568/832 |
| 4,634,668 | 1/1987 | Hagedorn ............................... | 435/146 |
| 4,877,732 | 10/1989 | Schofield ............................... | 435/155 |
| 5,284,759 | 2/1994 | Mader et al. ........................... | 435/125 |
| 5,449,830 | 9/1995 | Verhoeven et al. . | |

FOREIGN PATENT DOCUMENTS

| | | |
|---|---|---|
| 0 076 606 | 4/1983 | European Pat. Off. . |
| 0098137 A2 | 11/1984 | European Pat. Off. . |
| WO 95/24374 | 9/1995 | WIPO . |
| WO96/12818 | 2/1996 | WIPO . |
| 96/11282 | 4/1996 | WIPO . |
| WO 97/00966 | 9/1997 | WIPO . |

OTHER PUBLICATIONS

Warhurst et al., Biotransformations Catalyzed by the Genus Rhodococcus, (1994), Critical Rev. in Bioctechnology 14(1): pp. 29–73.

Gao, et al., Synthesis and Separation of Optically Active Compounds, (1994), Ann. pharmaceutiques francaises, 52, No. 4, pp. 184–203.

Martinez, et al. An Improved Modification of Ritter Reaction, (1989), Tetrahedron Letters, vol. 30, No. 5, pp. 581–582.

Wang, et al., Sequence and expression of the bpd C1C2BADE genes involved in the initial steps of biphenyl/chlorobiphenyl degardation by Rhodococcus sp. M5, (1995) Gene, 164, pp. 117–122.

Sitaram, et al., The Ion–Pair Extraction, Purification, and Liquid Chromatographic Analysis of Indolealkylamines in Human Urine, (1983), Analytical Biochemistry 128, pp. 11–20.

Brandstrom, et al., Ion Pair Extraction in Preparative Organic Chemistry, A Convenient Method for the Preparation of Salts of Amines, (1969), Acta Chem. Scand., 23, No. 4 pp. 1215–1218.

Bezborodov, et al, New strain of Rhodococcus crythropolis bacteria, (1993) WPI No. 93–318308 (Title only of SU 1752767).

Gibson, D.T., et al., Chemical Abstracts, No. 50834, vol. 125, No. 5 (1995).

Allen, et al., Enantioselective bacterial biotransformation routes to CIS–DIOL Metabolites of Monosubstituted Benzenes, Naphthalene and Benzocycloalkenes of Either Absolute Configuration, J. Chem. Commun, pp. 117–188 (1995).

Ascon–Cabrera, et al., Selection of Xenobiotic–Degrading Microogranisms in a Biphasic Aqueous–Organic System, Applied and Environmental Microbiology, vol. 59, No. 6, pp. 1717–1724 (1993).

Gibson, et al., Biotransformations Catalyzed By Toluene Dioxygenase From Pseudomonas Putida F1, In Pseudomonas: Biotransformations: Pathogenesis and Evolving Biotechnology. American Society For Microbiology, Washington, D.C., (S. Silver et al Eds. 1990), pp. 121–132.

Brand, et al., Sterospecific Hydroxylation of Indan by *Escherichia coli* Containing the Cloned Toluene Dioxygenase Genes From Pseudomonas Putida F1 Applied and Environmetnal Microbiology, vol. 58, No. 10, pp. 3407–3409 (1992).

Gibson, et al., Oxidative Degradation of Aromatic Hydrocarbons by Microoogrganisms, I. Enzymatic Formation of Catechol From Benzene Biochemistry, vol 7, No. 7, pp. 2653–2662 (1968).

Wacket, et al., Benzylic Monooxygenation Catalyzed by Toluene Dioxygenase From Psudomona Putida, Biochemistry, vol. 27, No. 4, pp. 1360–1367 (1988).

*Primary Examiner*—Sandra E. Saucier
*Attorney, Agent, or Firm*—Kenneth R. Walton; Melvin Winokur

[57] ABSTRACT

A process is disclosed that bioconverts indene to (1S)-amino-(2R)-indanol substantially free of any of its stereoisomers, by the action of the enzyme dioxygenase, followed by various chemical step(s), e.g., chiral specific crystallization, treatment with strong acid in the presence of acetonitrile.

1 Claim, No Drawings

PSEUDOMONAS PUTIDA STRAIN WITH DIOXYGENASE ACTIVITY

Provisional Application 60/600,360 filed Jun. 26, 1995.

BACKGROUND OF THE INVENTION

The present application is related to Merck 18996, U.S. Ser. No. 08/059,038, filed May 7, 1993, 18996IA, U.S. Ser. No. 08/235,576, filed Apr. 29, 1994, Merck 19251, Merck 19114, Merck 19115, and 19351.

The present invention is concerned with a process for synthesizing intermediates for compounds which inhibit the protease encoded by human immunodeficiency virus (HIV), and in particular certain oligopeptide analogs, such as Compound J in the Examples below. These compounds are of value in the prevention of infection by HIV, the treatment of infection by HIV and the treatment of the resulting acquired immune deficiency syndrome (AIDS). These compounds are also useful for inhibiting renin and other proteases.

The inventions described herein concern the conversion of indene to (2S)-amino-(1R)-indanol as illustrated by the following Schemes, I, II & III.

SCHEME I

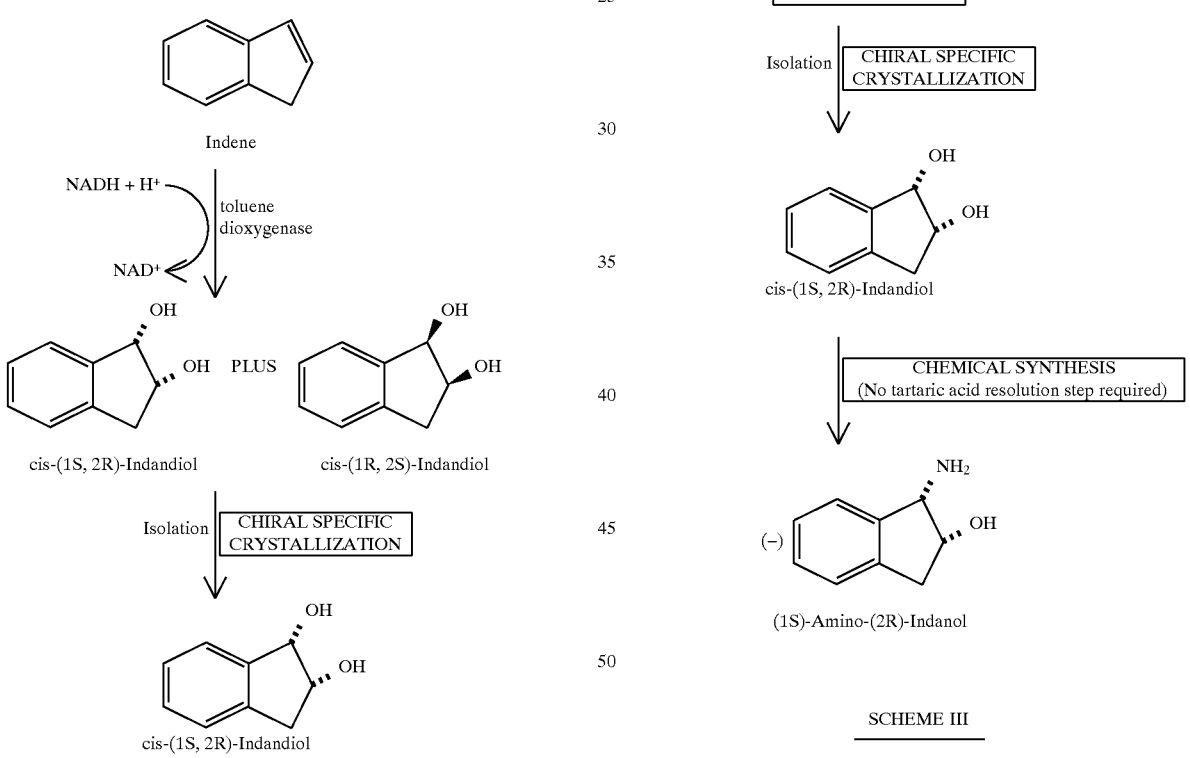

SCHEME II

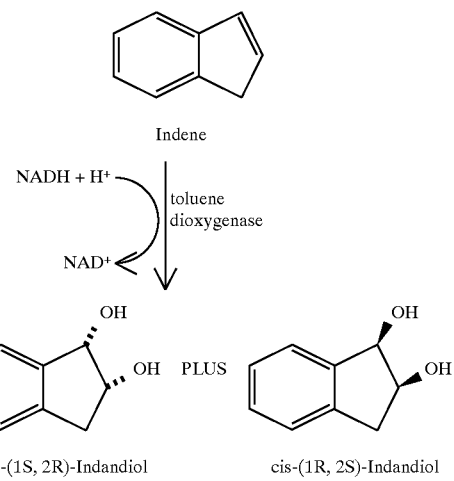

SCHEME III

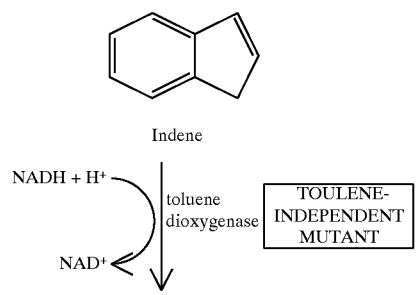

-continued
SCHEME III

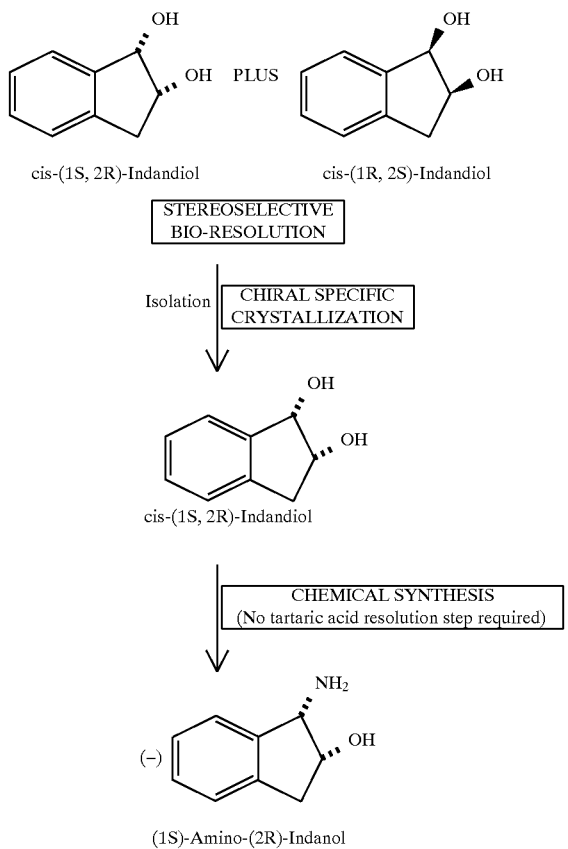

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., *Proc. Nat'l Acad. Sci.*, 85, 4686 (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ratner, L. et al., *Nature*, 313, 277 (1985)]. Amino acid sequence homology provides evidence that the pol sequence encodes reverse transcriptase, an endonuclease and an HIV protease [Toh, H. et al., *EMBO J.*, 4, 1267 (1985); Power, M. D. et al., *Science*, 231, 1567 (1986); Pearl, L. H. et al., *Nature*, 329, 351 (1987)]. The end product compounds, including certain oligopeptide analogs that can be made from the novel intermediates and processes of this invention, are inhibitors of HIV protease, and are disclosed in EPO 541,168, which published on May 12, 1993. See, for example, Compound J therein, also illustrated in the Examples below.

The present application discloses an improved process to make, in substantial stereoisomeric purity, 1(S)-amino-2(R)-hydroxy indan of the structure

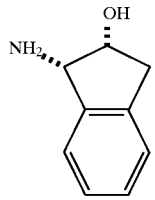

which is a sidechain group of Compound J, which is a potent inhibitor of HIV protease.

Previous attempts at synthesis involve inefficient production of the racemate 1(±)-amino-2(±) hydroxy indan from the racemic indene oxide. Other attempts at synthesis involve bioconversion of indene with a fungal haloperoxidase to give predominantly trans-(2S,1S)-bromoindanol, which is then subjected to various chemical steps to give (1S)-amino-(2R)-indanol. Still other attempts at synthesis relate to chemical synthesis with racemic epoxidation as an intermediate step, followed by resolution with L-tartaric acid.

The present invention provides needed improved alternatives. In the processes of the present invention, the tartaric acid resolution step is eliminated by combining stereoselective bio-oxidation of substrate indene to cis (1S,2R)-indandiol with subsequent isolation of substantially stereoisomerically pure cis-(1S,2R)-indandiol crystals by the technique of chiral specific crystallization. Further chemical treatment gives (1S)-amino-(2R)-indandiol, e.g. treatment with a nitrile in the presence of aqueous acid according to the Ritter reaction, followed by either reverse ion pair extraction or cation exchange chromatography.

In the processes of the present invention, indene is converted by the action of the enzyme dioxygenase to a mixture of cis indandiols containing predominantly the desired (1S, 2R) stereoisomer. The desired (1S,2R) stereoisomer is isolated using purification steps, e.g., adsorption, extraction, crystallization to yield substantially pure crystallized cis(1S, 2R)-indandiol.

An enantiomeric excess of over about 99% (from indene to the substantially pure cis-(1S,2R)-indandiol after chiral specific crystallization) is typical of the processes of the present invention.

BRIEF DESCRIPTION OF THE INVENTION

The present invention provides new methods to effect the synthesis of cis-(1S,2R) indandiol, by bioconversion by the action of the enzyme dioxygenase. The intracellular expression of dioxygenase may be induced by toluene (toluene dioxygenase) or its intracellular expression may be toluene independent. Subsequent chemical steps permit formation of (1S)-amino-(2R)-indanol, another intermediate. These product compounds are intermediates for compounds useful in the synthesis of inhibitors of HIV protease, renin and other proteases, e.g., Compound J.

DETAILED DESCRIPTION OF THE INVENTION

The present invention is concerned with a process for synthesizing intermediates for compounds which inhibit the HIV protease. One desired intermediate is (1S)-amino-(2R)-indanol substantially free of its undesired stereoisomers. Another desired intermediate is (1S,2R)-indandiol substantially free of its undesired stereoisomer (1R,2S)-indandiol.

In this invention, a process is described for synthesizing (1S,2R)-indandiol, comprising the steps of:
   a) contacting a quantity of toluene dioxygenase with a quantity of indene;
   b) fermenting the resulting mixture;
   c) to give (1S,2R)-indandiol.

Another process is described for synthesizing (1S,2R)-indandiol substantially free of any stereoisomer, comprising the steps of:
   a) contacting a quantity of toluene dioxygenase with a quantity of indene;
   b) fermenting the resulting mixture;
   c) purifying (1S,2R)-indandiol;
   d) subjecting the product of Step c) to chiral specific crystallization;
   e) to give (1S,2R)-indandiol substantially free of any stereoisomer.

Another process is described for synthesizing (1S,2R)-indandiol, comprising the steps of:
   a) contacting a quantity of dioxygenase with a quantity of indene;
   b) fermenting the resulting mixture;
   c) to give (1S,2R)-indandiol.

Another process is described for synthesizing (1S,2R)-indandiol substantially free of any stereoisomer, comprising the steps of:
   a) contacting a quantity of dioxygenase with a quantity of indene;
   b) fermenting the resulting mixture;
   c) purifying (1S,2R)-indandiol;
   d) subjecting the product of Step (c) to chiral specific crystallization;
   e) to give (1S,2R)-indandiol substantially free of any stereoisomer.

Another process is described for synthesizing (1S)-amino-(2R)-indanol substantially free of any stereoisomer, comprising the steps of:
   a) contacting a quantity of toluene dioxygenase with a quantity of indene;
   b) fermenting the resulting mixture;
   c) purifying (1S,2R)-indandiol;
   d) subjecting the product of Step (c) to chiral specific crystallization;
   e) to give (1S,2R)-indandiol substantially free of any stereoisomer;
   f) dissolving one equivalent of the (1S,2R)-indandiol of step e) in excess acetonitrile to give a second mixture, and maintaining the second mixture between about −40° C. and about 25° C.;
   g) mixing thereto excess equivalents of strong acid, and maintaining the reaction at between about −40° C. and about 25° C.;
   1h) to give (1S)-amino-(2R)-indanol substantially free of any stereoisomer.

Another process is described for synthesizing (1S)-amino-(2R)-indanol substantially free of any stereoisomer, comprising the steps of:
   a) contacting a quantity of dioxygenase with a quantity of indene;
   b) fermenting the resulting mixture;
   c) purifying (1S,2R)-indandiol;
   d) subjecting the product of Step c) to chiral specific crystallization;
   e) to give (1S,2R)-indandiol substantially free of any stereoisomer;
   f) dissolving one equivalent of the (1S,2R)-indandiol of step e) in excess acetonitrile to give a second mixture, and maintaining the second mixture between about −40° C. and about 25° C.;
   g) mixing thereto excess equivalents of strong acid, and maintaining the reaction at between about −40° C. and about 25° C.;
   h) to give (1S)-amino-(2R)-indanol substantially free of any stereoisomer.

Another process is described for bio-resolution for removing cis-(1R,2S)-indandiol from a mixture of cis-(1S,2R)-indandiol and cis-(1R,2S)-indandiol, comprising the steps of:
   a) contacting a quantity of dihydrodiol dehydrogenase with a mixture of cis-(1S,2R)-indandiol and cis-(1R, 2S)-indandiol;
   b) fermenting the resulting mixture;
   c) to give cis-(1S,2R)-indandiol substantially free of the stereoisomer cis-(1R,2S)-indandiol.

A pure culture of *Pseudomonas putida* 421-5, ATCC 55687 is also described.

Further purification of (1S)-amino-(2R)-indanol may be achieved by reverse ion pair extraction or, alternatively, cation exchange chromatography.

One preferred source of toluene dioxygenase is *Pseudomonas putida* F1, deposited at the ATCC with access number 55688.

One preferred source of toluene-independent dioxygenase or dioxygenase is *Pseudomonas putida* 421-5, deposited at the ATCC with access number 55687.

Preferred sources of dihydrodiol dehydrogenase are *Pseudomonas putida* F1, deposited at the ATCC with access number 55688, or *Pseudomonas putida* 421-5, deposited at the ATCC with access number 55687.

In the bioconversion of indene to a mixture of cis-(1S, 2R)-indandiol and cis-(1R,2S)-indandiol, any enzyme that dihydroxylates is suitable. Preferred enzymes include those giving substantial stereoisomeric excess of the (1S,2R) stereoisomer, e.g., toluene dependent dioxygenase (also known as toluene dioxygenase) or toluene independent dioxygenase. Applicants have isolated a toluene independent mutant *Pseudomonas putida* strain 421-5, which constitutively expresses the dioxygenase enzyme. Such strain eliminates the process steps for toluene induction of the enzyme.

Applicants have also discovered that simultaneous stereoselective bio-resolution occurs during fermentation of *Pseudomonas putida* with indene. This bio-resolution degrades, by the action of the enzyme dihydrodiol dehydrogenase, unwanted stereoisomer cis-(1R,2S)-indandiol, thus boosting the stereoisomeric excess of desired stereoisomer cis-(1S,2R)-indandiol. Any enzyme that specifically degrades the cis-(1R,2S)-indandiol is suitable for stereoselective bio-resolution.

Fermentation of indene with a microrganism containing dioxygenase, and optionally dihydrodiol dehydrogenase, is conducted in the presence of an oil reservoir for the indene, e.g., silicone oil. The oil reservoir for indene avoids the toxicity to cells of high concentrations of indene. The preferred microorganism for such fermentations is *Pseudomonas putida*, most preferably ATCC 55688 and 55687. Other suitable microorganisms include *E.coli* transformed with genes for the relevant enzymes, including genes for *Pseudomonas putida* toluene dioxygenase and optionally *Pseudomonas putida* dihydrodiol dehydrogenase.

After fermentation, the fermentation mixture is spun down or centrifuged to give three layers. There is a top layer of the oil reservoir, typically silicone oil, then a middle aqueous layer with the desired indandiol bioconverted products, and a bottom layer of cells and debris. The middle layer is subjected to further treatment.

The middle aqueous layer is then mixed with a hydrophobic resin to bind the indandiol products. Suitable hydrophobic resins include, but are not limited to, styrene-divinyl benzene resin, reverse phase C18 resin, or uncharged acrylic resins.

After washing the resin with water or other suitable aqueous solvent, the resin is eluted to remove bound indandiol with eluting solvent. Eluting solvents include any organic solvent, preferably a mixture of acetonitrile and water, most preferably a mixture of about 20%(v/v) acetonitrile and about 80%(v/v) water. The eluting solvent must be immiscible with the extraction solvent for chiral specific crystallization.

Eluted indandiol is typically concentrated, then subjected to chiral specific crystallization. In this process, an extraction solvent is added, mixed with indandiol in eluting solvent, then the extraction solvent layer saved. Subsequent removal of water from the extraction solvent layer will crystallize out cis-(1S,2R)-indandiol, affording chiral specific crystallization. Suitable extraction solvents include isopropyl acetate, toluene, or many other organic solvents, preferably isopropyl acetate. After addition of the extraction solvent, water is removed by vacuum concentration.

Chiral specific crystallization can be used instead of, or in conjunction with, stereoselective bio-resolution, to enhance stereoisomeric excess of desired product cis-(1S,2R)-indandiol substantially free of any stereoisomer.

ATCC Deposits

Before the U.S. filing date of the present application, samples of the microorganism MB5612 and MB5652 were deposited at the American Type Culture Collection (ATCC), 10801 University Boulevard, Manassas, Va. 20110. The culture access designations are ATCC 55688 and 55687, respectively. This deposit will be maintained in the ATCC for at least 30 years and will be made available to the public upon the grant of a patent disclosing it. It will be understood that the availability of a deposit does not constitute a license to practice the subject invention in derogation of patent rights granted by government action.

General Characteristics of ATCC 55688 and 55687

The physical characteristics and taxonomy, including morphological, cultural, biological and physiological characteristics are briefly described hereinbelow.

MB5612—(strain F1) ATCC 55688 The culture was received as a serial transfer of *P. putida* DSM6899. It is motile, oxidase positive, Gram negative rod, 0.38×0.76 mm with blunt ends, tending to ovoid. Good to excellent growth observed on trypticase soy agar (TSA), eosin-methylene blue agar (EMB), MacConkey's agar, sheep blood agar and Sabouraud maltose agar (SMA) at 28° and 37° C. On TSB colonies were transparent, raised and had an entire edge. Colony texture was butyrous and the surface glistened. No diffusible pigments were observed. Putrid odor. On blood agar the cultures were γ-hemolytic. Biochemical reactions observed in the API Rapid NFT panel were as follows: positive for arginine dihydrolase, negative for nitrate, tryptophane, glucose fermentation, urease, and hydrolysis of esculin, gelatin and p-nitro-phenyl-β-D-galactopyranoside. Positive for oxidative utilization of glucose, manose (48 h), gluconate, caprate malate citrate and phenyl-acetate. When these characteristics were scored according to the instructions the most probable identification of the organism was *P. putida* (P=0.998). Analysis of whole cell fatty acids, as methyl esters, by gas-liquid chromatography (FAME analysis) revealed a lipid composition consistent with those of Gram negative bacteria, rich in unsaturated, monounsaturated and cyclopropane fatty acids. Low concentrations of hydroxylated fatty acids were also found observed. Comparison of the chromatograms for this organism against the MIDI database yielded an excellent match for *P. putida* biotype A (similarity=0.913, MIDI Clinical Library, Ver 3.6).

MB5652—(strain 421-5) ATCC 55687 This culture was received as an isolate derived from MB5612. On plating (TSA) two colony types were observed. A large, shiny white colony with a transparent edge and raised center and a smaller, tan colored variant that is transparent to opaque with a raised center and transparent edge. Both colony variants were observed on other media as well. Gram stains of the two colony types reveal that the cells in the large colonies are Gram negative rods 0.76×1.5–3.4 μm. Cells from the small colony type were also Gram negative but appeared swollen and variable in width (0.76×1.14×1.9–3.4 μm). Both colony variants had virtually identical biochemical profiles to the parent strain (MB5612) in the API Rapid NFT panel. The FAME profiles of the two colony variants were essentially identical to one another. These differed from the parent strain, having slightly elevated concentrations of 17:0 cyclopropane (approximately 35%) and slightly decreased concentrations of 16:1 ω7c (approximately 11%). These observed differences did not, however, effect the identification of the two colony variants as strains of *P. putida* biotype A (similarity 0.885 and 0.895 for the large and small colony types respectively).

General Description Of Culture Conditions

The preferred source of carbon in the nutrient medium are carbohydrates such as glucose, xylose, galactose, glycerin, starch, dextrin, and the like. Other sources which may be included are maltose, rhamnose, raffinose, arabinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates, and yeast hydrolysates, corn steep liquor, dried yeast, wheat germ, feather meal, peanut powder, distiller's solubles, etc., as well as inorganic and organic nitrogen compounds such as ammonium salts (e.g., ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

As to the conditions for the production of cells in massive amounts, submerged aerobic cultivation conditions are preferred. For the production in small amounts, a shaking culture in a flask is employed. Furthermore, when the growth is carried out in large tanks, it is desirable first to produce an inoculum of the organism by inoculating a relatively small quantity of culture medium with the organism stored at −20° to −70° C. and culturing said inoculated medium, also called the "seed medium", and then to transfer the resulting inoculum aseptically to large tanks. The fermentation medium, in which the inoculum is produced, is generally autoclaved to sterilize the medium prior to inoculation. The pH of the medium is generally adjusted to about 7.0 prior to the autoclaving step.

Agitation and aeration of the culture mixture may be accomplished in a variety of ways. Agitation may be provided by impeller or similar mechanical agitation equipment, shake flask bioreactor, by various pumping equipment or by the passage of sterile air through the medium. Aeration may be effected by passing sterile air through the fermentation mixture.

The fermentation is usually conducted at a temperature between about 25° C. and 37° C., preferably 30° C., for a period of about 0.5 to 5 days, preferably 2, which may be varied according to fermentation conditions and scales. Preferably, the production cultures are incubated for about 2 days at 30° C. in a stirred bioreactor operating at an impeller speed of about 300 rpm.

Preferred culturing/production media for carrying out the fermentation include the following media:

TABLE 1

Media composition for indene bioconversion by *P. putida* Fl (modified from Finette et. al., Journal of Bacteriology 160, 1004 (1984). All values are per Liter.

| Material | Seed | Production |
| --- | --- | --- |
| L-arginine | 2.00 g | 4.00 g |
| $(NH_4)_2SO_4$ | 1.00 g | 2.00 g |
| $Na_2HPO_4$ | 5.24 g | 10.48 g |
| $KH_2PO_4$ | 2.77 g | 5.54 g |
| $MgSO_4$—$7H_2O$ | — | 0.58 g |
| $CaCl_2$—$2H_2O$ | — | 0.13 g |
| $(NH_4)_6Mo_7O_{24}$—$4H_2O$ | — | 0.36 mg |
| $FeSO_4$—$7H_2O$ | — | 3.96 mg |
| Modified Hutners mineral base * | 20 mL | — |
| Modified Metals 44 ** | — | 2.00 mL |
| silicone oil | — | 200 mL |
| defoamer | — | 1.00 mL |

Adjust pH to 7.0 with 6M sulfuric acid
* Modified Hutner's mineral base: EDTA, 10 g; $MgSO_4$—$7H_2O$, 14.45 g; $CaCl_2$—$2H_2O$, 3.33 g; $(NH_4)6Mo$—$_7O_{24}$—$4H_2O$, 0.009 g; $FeSO_4$—$7H_2O$, 0.099 g; metals 44, 50 mL; distilled water to 1 Liter; pH adjusted to 6.6–6.8 with 6M sulfuric acid.
** Modified Metals 44 (in milligrams per 100 mL): EDTA, 250; $ZnSO_4$—$7H_2O$, 1,095; $FeSO_4$—$7H_2O$, 500; $MnSO_4$—$H_2O$, 154; $CuSO_4$—$5H_2O$, 39.2; $CoCl_2$—$6H_2O$, 24.8; $Na_2B_4O_7$—$10H_2O$, 17.7; add about 0.400 mL 6M sulfuric acid to retard precipitation.

Preferred conditions for operating the fermentor during fermentation include the following parameters.

TABLE 2

Fermentor conditions.

| Process variable | Set point |
| --- | --- |
| temperature | 30° C. |
| pH | 7.0 |
| agitation | 300 RPM |
| air flow | 20 Liters/minute |
| pressure | 0.3 bar |

Further Steps After Fermentation
Silicone oil Removal

The whole broth is transferred from the fermentor to a harvest tank and allowed to settle a minimum of 4 hours. Usually settling is done overnight. After settling, the lower aqueous phase containing the cis-indandiol and fermentation solids is transferred to the column feed tank. The upper organic layer is discarded.

Expanded Bed Adsorption

The aqueous phase is then pumped into the bottom and out the top of a column of brominated styrene divinylbenzene resin with density greater than 1.1. The expanded bed operation allows cis-indandiol to be adsorbed onto the resin while the fermentation solids pass through the column unretained. After loading, the resin is washed with de-ionized water in the upflow direction to displace residual fermentation solids and spent aqueous feed. Resin is washed with one column volume of 20% v/v acetonitrile/80% v/v water eluant in the upflow direction and then the cis-indandiol is eluted in the downflow direction with 20% v/v acetonitrile/80% v/v water eluant in the downflow direction. The eluate is collected in fractions and individually assayed by HPLC for cis-indandiol concentration.

Vacuum Concentration/Isopropyl Acetate Extraction

The pooled eluate fractions containing ~80% of the cis-indandiol are vacuum concentrated to reduce the volume and reduce the acetonitrile content. An equal volume of isopropyl acetate is added to the concentrate and agitated for a minimum of 5 minutes. The phases are then settled by gravity for minimum of 2 hours. The upper organic phase is removed and then the lower aqueous phase is extracted three more times with an equal volume of isopropyl acetate.

Vacuum Concentration/Chiral Specific Crystallization

This crystallization step serves two critical purposes. One purpose is to increase chemical purity by rejecting other indene metabolites such as indenol and indanone that are carried through the initial isolation steps. The other purpose is to increase the chiral purity by the rejection of the undesired 1R,2S stereoisomer in the mother liquors. The crystallization is as follows:

The combined isopropyl acetate extracts are vacuum concentrated to ~30 g cis-indandiol/liter and then filtered through a medium porosity glass filter to remove any particulate. The filtered extract is then further concentrated to a final concentration of 200 g cis-indandiol/liter. The cis-indandiol begins to crystallize during the final concentration step and the crystallization is completed by cooling to 5+–0° C. and aging a minimum of 8 hours. The crystals are filtered, washed with isopropyl acetate/hexane (1:1), then hexane, and dried under vacuum. Typical yield is 45% from whole broth to cis-indandiol with >99.5% stereoisomer excess of the 1S,2R form.

Product Recovery

The product cis-(1S,2R) indandiol is found in the aqueous phase of the media, and accordingly can be isolated and purified by conventional methods such as centrifugal or gravitational clarification of the aqueous phase, concentration under reduced pressure, extraction with a conventional solvent, such as isopropyl acetate and the like, pH adjustment, treatment with a conventional resin (e.g., anion or cation exchange resin, non-ionic resin, etc.), treatment with a conventional adsorbent (e.g., activated charcoal, silica gel, cellulose, alumina, etc.), crystallization, recrystallization, and the like.

The preferred sequence of methods includes aqueous phase clarification, product adsorption onto a resin and elution using an aqueous solvent mixture, concentration of richcuts under reduced pressure, solvent extraction of product, solvent concentration under reduced pressure, and crystallization.

Conversion of cis-(1S,2R)-indandiol to cis-(1S)-Amino-2R-Indanol

Reaction of the cis-(1S,2R)-indandiol with acetonitrile, followed by hydrolysis in the presence of water, is carried out rapidly. One equivalent of solid cis-(1S,2R)-indandiol is dissolved in excess acetonitrile, with or without organic solvent. A typical solvent is dichloromethane. The mixing of the diol with acetonitrile is exothermic, so cooling is typically carried out before contacting with strong acid.

The mixture of cis-(1S,2R)-indandiol and acetonitrile is then contacted with excess equivalents of strong acid, such as triflic acid, methanesulfonic acid or sulfuric acid. Typically about two equivalents of strong acid are added. After about one or two hours, excess water equivalents are added. The remaining acetonitrile is removed by distillation or refluxing, to give a Ritter solution.

The resulting cis-(1S)-amino-(2R)-indanol is substantially free of the stereoisomer trans-aminoindanol. Typically, resolution is not needed in subsequent steps.

Purification of cis-(1S)-amino-(2R)-indanol

The Ritter solution then may be subjected to various treatments to remove acid contaminants.

A. Reverse Ion Pair Extraction

Base is added to neutralize the acid, then to raise the pH to about 12 or higher, to give a basified Ritter solution. This basified Ritter solution is extracted with any organic solvent having a suitable solubility for cis-aminoindanol; e.g. methylene chloride, ethyl acetate or 1-butanol, preferably 1-butanol. The aqueous layer(s) then may be discarded.

To the organic layer(s) containing cis-aminoindanol is added a suitable acid in excess of cis-aminoindanol equivalents. Suitable acids will form a salt complex with cis-aminoindanol and make the cis-aminoindanol more soluble in aqueous solution. Such suitable acids include but are not limited to L-tartaric, D-tartaric, meso-tartaric, ascorbic, malonic, citric, formic acids, HCl, preferably L-tartaric acid.

The resulting salt in organic solvent is then extracted with an aqueous solution, e.g. water, to give an aqueous extract. Titration of base equivalents into the aqueous extract will give crystallization beginning at about pH 8-9. Crystallization is typically complete before titration with base reaches pH of about 11-12. The resulting (IS)-amino-(2R)-indanol is substantially pure.

B. Cation Exchange Chromatography

Alternatively, the Ritter solution may be subjected to cation exchange chromatography to remove acid contaminants. Any cation exchange resin is suitable, but typically comprises styrene-divinylbenzene resin, attached thereto with acid groups, such as sulfonic acid or carboxylic acid.

The resin is mixed with the Ritter solution, then washed with water or other aqueous solvent to remove unwanted acid. The bound cis-aminoindanol is eluted by the steps of adding base (to increase pH to keep cis-aminoindanol soluble), followed by elution with any one of a variety of solvents, e.g. methanol, acetonitrile or THF in water. The basification-elution cycle may be repeated several times to quantitatively elute cis-aminoindanol off the resin. The resulting (1 S)-amino-(2R)-indanol is substantially pure.

Formulations

The product compounds synthesized from the intermediates of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

The processes and intermediates of this invention are useful for the preparation of end-product compounds that are useful in the inhibition of HIV protease, the prevention or treatment of infection by the human immunodeficiency virus (HIV), and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the end-product compounds that can be made from the processes and intermediates of this invention are useful in treating infection by HIV after suspected past exposure to HIV by, e.g., blood transfusion, organ transplant, exchange of body fluids, bites, accidental needle stick, or exposure to patient blood during surgery.

The end-product HIV protease inhibitors are also useful in the preparation and execution of screening assays for antiviral compounds, including their use as controls. For example, end-product compounds are useful for isolating enzyme mutants, which are excellent screening tools for more powerful antiviral compounds. Furthermore, such compounds are useful in establishing or determining the binding site of other antivirals to HIV protease, e.g., by competitive inhibition. Thus the end-product compounds that are made from the processes and intermediates of this invention are commercial products to be sold for these purposes.

The end product HIV protease inhibitor Compound J has the structure

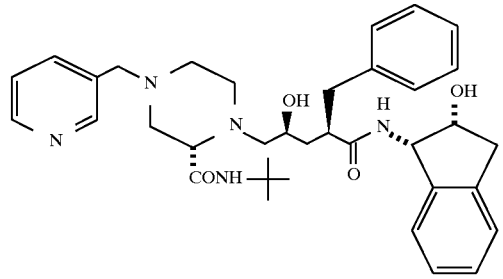

or pharmaceutically acceptable salts or hydrates thereof. Compound J is named

N-(2(R)-hydroxy-1(S)-indanyl)-2(R)-phenylmethyl-4(S)-hydroxy-5-(1-(4-(3-pyridylmethyl)-2(S)-N'-(t-butylcarboxamido)-piperazinyl))pentaneamide;

[1S-[1α[αS*,γR*,δ(R*)],2α]]-N-(2,3-dihydro-2-hydroxy-1H-inden-1-yl)-2-[[(1,1 -dimethylethyl)amino]carbonyl]-γ-hydroxy-α-(phenylmethyl)-4-(3-pyridinylmethyl)-2-piperazinepentaneamide; or N-(1(S)-2,3-dihydro-2(R)-hydroxy-1H-indenyl)-4(S)-hydroxy-2(R)-phenylmethyl-5-[4-(3-pyridylmethyl)-2(S)-t-butylcarbamoyl)piperazinyl]pentaneamide.

HIV protease inhibitor compounds that can be made from the intermediates and processes of the instant invention are disclosed in EPO 541,168. The HIV protease inhibitory compounds may be administered to patients in need of such treatment in pharmaceutical compositions comprising a pharmaceutical carrier and therapeutically-effective amounts of the compound or a pharmaceutically acceptable salt thereof. EPO 541,168 discloses suitable pharmaceutical formulations, administration routes, salt forms and dosages for the compounds.

The compounds of the present invention, may have asymmetric centers and occur as racemates, racemic mixtures and as individual diastereomers, or stereoisomers with all isomeric forms being included in the present invention. A mixture of stereoisomers includes a 1:1 mixture, as well as any other mixture, e.g., 1:4, 4:3, 2:1.

Representative experimental procedures utilizing the novel process are detailed below. These procedures are exemplary only and are not limitations on the novel process of this invention.

EXAMPLE 1

Protocol For *P. putida* F1

A. Reverse phase analysis of substrate and products

Two parts of isopropyl alcohol (IPA) were added to one part of whole broth. The mixture was shaken for 1 minute and then centrifuged at 5000 rpm for 15 minutes to pellet the cells and separate the oil (bottom phase) from the IPA/water phase (top layer). An aliquot of the top layer was injected on a C18 reverse phase HPLC column (250×4.6 mm) attached to an HPLC system.

B. Chiral assay of cis-1,2-indandiol

After allowing phase separation of the whole broth (~10 minutes gravity settling), 5 mL of the aqueous phase (bottom) was added to 10 mL ethyl acetate (EthAc). A 5-mL aliquot of the EthAc layer (top) was dried under a nitrogen sweep. The EthAc extracted compounds were then resuspended in a 95% hexane: 5% ethanol solution and injected onto a chiral column (250×4.6 mm) attached to an HPLC system.

C. Seed development

Sections C-E in this Example were developed for 23 liter fermentors. A two-liter nonbaffled shake flask containing 500 mL of seed medium (Table 1, supra) was inoculated with 1 mL of starter culture. The seed flask was placed on a 200 RPM rotary shaker and cultivated at 30° C. When the culture reduced mid logarithmic growth (about 8 hours), 50 mL were transferred to the production vessel.

D. Induction

Toluene (75 g) was added to a stirred vessel containing 15 liters of production medium (Table 3). An LEL meter was connected to the off gas line to determine if the vapor emission by the fermentor was below the lower explosion limit (LEL) of toluene. The measurement taken just after toluene addition was about 30% of the LEL of toluene and represented the highest reading during the entire run. The fermentor was immediately inoculated with 50 mL from the seed flask of Section C. All fermentor parameters except pH were held constant throughout the run for both the induction and bioconversion stages (Table 4). After the overnight induction period (approximately 12 to 14 hours), the broth was light yellow and ready for indene addition.

TABLE 3

Media composition for indene bioconversion by *P. putida* F1 in 23-Liter stirred bioreactors (modified from Finette et al., Journal of Bacteriology, 160, 1984, pg 1004). All values are per Liter.

| Material | Production |
| --- | --- |
| L-arginine | 2.00 g |
| $(NH_4)_2SO_4$ | 1.00 g |
| $Na_2HPO_4$ | 5.24 g |
| $KH_2PO_4$ | 2.76 g |
| $MgSO_4$—$7H_2O$ | 0.29 g |
| $CaCl_2$—$2H_2O$ | 0.07 g |
| $(NH_4)_6Mo_7O_{24}$—$4H_2O$ | 0.17 mg |
| $FeSO_4$—$7H_2O$ | 1.93 mg |
| Hutners mineral base* | — |
| Metals 44** | 1.00 mL |
| silicone oil | 200 mL |
| defoamer | 1.00 mL |

Adjust pH to 7.0 with 6M sulfuric acid

TABLE 4

Fermentor Conditions

| Process variable | Set point |
| --- | --- |
| temperature | 30° C. |
| pH | 7.0 |
| agitation | 300 RPM |
| air flow | 5.0 L/minute |
| pressure | 0.3 bar |

E. Bioconversion

Indene was added directly to the vessel to a final concentration of 1.0 g/L to initiate the bioconversion. The fermentation was monitored at 30–60 minute intervals for total product formation as well as optical activity of the cis-1,2-indandiol. The cis-1,2-indandiol concentration plateaued at about 200 mg/L in about four hours. The stereoisomeric excess EE for cis-1S,2R-indandiol continued to increase from <60% to >98% even though the bioconversion from indene to the cis-1,2-indandiol stops. The dissolved oxygen of the vessel dropped during the fermentation, reaching 40% saturation as the lowest measured value. After the eight-hour bioconversion period, 52% of the indene was utilized, reaching a 39% conversion yield on the product's optical purity. The fermentation was monitored at 30–60 minute intervals for total product formation as well as optical activity of the cis-1,2-indandiol. After the eight-hour bioconversion period, 62% of the indene was utilized, reaching a 35% conversion yield. The fermentor was chilled to 15° C. prior to clarification of the aqeuous layer.

EXAMPLE 2

Protocol For F1; Scale Up to 70-Liter Fermentors

A. Seed development

A two-liter nonbaffled shake flask containing 500 mL of seed medium (Table 1) was inoculated with 1 mL of starter culture. The flask was placed on a 200 RPM rotary shaker and cultivated at 30° C. After eight hours of incubation, the culture reached an optical density (600 nm) of 0.6 to 0.7, and was ready for transfer to the production vessel.

B. Induction

Toluene (250 g) was added to a stirred vessel containing 50 liters of production medium (Table 1). As with the smaller fermentor, an LEL meter was connected to the off gas line to determine if the vapor emission by the fermentor was below the LEL of toluene. The measurement taken just after toluene addition was again about 30% of the LEL of toluene and represented the highest reading during the entire run. The fermentor was immediately inoculated with the entire contents of the seed flask (section C). The fermentor parameters, except pH, were held constant throughout the run for both the induction and bioconversion stages (Table 2). After the overnight induction period (approximately 12 to 14 hours), the broth was light yellow and ready for indene addition.

C. Bioconversion

Indene was added directly to the vessel to a final concentration of 2.5 g/L to initiate the bioconversion. The indene purity (technical grade, 90% vs. reagent grade, 99+%) appeared to have little to no effect on the product's optical purity. The fermentation was monitored at 30–60 minute intervals for total product formation as well as optical activity of the cis-1,2-indandiol. The cis-1S,2R-indandiol concentration plateaued between 500 to 700 mg/L in about 6 hours. The EE for cis-1S,2R-indandiol continued to increase from <60% to almost 80%. The pH at this scale never dropped below 6.5 or rose above 7.5 under the stated conditions although no pH control was used. As with the 23-liter fermentor, dissolved oxygen dropped during the fermentation, but not below 40% saturated DO. After the eight-hour bioconversion period, 62% of the indene was utilized, reaching a 35% conversion yield. The fermentor was chilled to 15° C. prior to clarification of the aqueous layer.

D. Aqueous layer clarification

The fermentor agitator was stopped and contents were settled for a minimum of 4 hours. The lower aqueous layer was cut to jugs. Volume of aqueous layer and concentration of the cis-indandiol were 37 liters and 0.45 g/l, respectively. DI water (19 liters) was added to fermentor and agitated for 10 minutes and then settled overnight. The second lower aqueous layer was again cut to jugs. Volume and cis-indandiol concentration of second aqueous layer was 21 liters and 0.05 g/l, respectively. The silicone oil layer was cut to jugs for disposal. Cells were separated from the aqueous layer by centrifugation in 400 mL bottles. Centrifugation was done at 8000 rpm for 45 minutes at 5° C.

E. Resin adsorption

The clarified first aqueous layer was fed to a column at ~25 mL/min. The column contained 260 mL of styrene-divinyl benzene type resin (bed height 21.5 inches). The aqueous layer was charged until product concentration in the effluent was equal to 25% of inlet product concentration. There was no detectable product in the first ten liters of effluent then the product concentration in the effluent rose sharply to 0.1 g/l within two more liters. Total aqueous layer fed was 48 bed volumes (12.9 liters). The column was washed with two bed volumes (450 mL) of DI water. The wash contained 0.12 grams of product (~2%). The column was then eluted using 3.3 bed volumes (900 mL) of 20% acetonitrile/80% water and 0.20 bed volume (50 mL) fractions were collected. The column was regenerated by washing with ~5 bed volumes of acetonitrile and then re-equilibrated by washing with several bed volumes of DI water.

F. Isopropyl acetate extraction

Combined richcuts were vacuum concentrated from 700 mL to 350 mL in the lab rotovap. An equal volume of isopropyl acetate was added to the concentrate and mixed for 5 minutes. Liquid phases were separated by gravity settling for at least 30 minutes. The extraction was repeated twice more to recover 94% of the product in the combined richcuts. The final combined isopropyl acetate volume was 1.05 liters.

G. Chiral specific crystallization with isopropyl acetate

The isopropyl acetate extracts were vacuum concentrated in the lab rotovap to 25 mL (diol concentration about 200 g/L). The concentrate was warmed to 60° C. to dissolve all solids, cooled to 55° C., and seeded with 0.025 grams (~0.5%) of diol crystals. Batch was then cooled slowly to 35° C. over a 4 hour period. It was cooled to 5° C. and aged overnight. Crystals were vacuum filtered on a sintered glass filter, washed with 5 mL of cold (5° C.) isopropyl acetate, and 10 mL of hexane. Drying was done under vacuum with no heat. Yield loss in the mother liquors was approximately 20%.

EXAMPLE 3

Biochemical resolution of racemic cis-1,2-indandiol

The ability of Pseudomonas putida F1 to biochemically resolve racemic cis-1,2-indandiol to optically active 1S,2R-indandiol was carried out by cultivating the organism in two 23-Liter reactors and inducing with toluene overnight as usual. Indene was added to one of the vessels to initiate the bioconversion. When bioconversion stopped (approx. three hours) in this vessel, cells from both vessels were pelleted, resuspended in spent medium from the vessel that received no indene, and transferred to 2-Liter non-baffled shake flasks to which 200 mg/L racemic cis-1,2-indandiol had been added. Spent medium from the culture not receiving indene and sterile seed medium+20% oil were run as controls. All flasks were placed on a reciprocal shaker (200 shakes per minute) and incubated at 30° C. The EE was measured at intervals up to 26 hours (Table 5). Samples were also analyzed by reversed phase HPLC to detect any possible metabolites derived from the apparent biochemical conversion of the undesirable cis-1,2-indandiol stereoisomer. After 26 hours of incubation, the EE measured in flasks containing cells was >98% in favor of the 1S,2R stereoisomer, regardless of whether the culture had been exposed to indene or not, whereas racemic cis-1,2-indandiol remained in the flasks absent of cells.

TABLE 5

Summary of resolution study.

| | Cells Present | | Cells Absent | |
|---|---|---|---|---|
| Condition | indene (+) | indene (−) | spent from indene (−) | sterile seed med. + oil |
| t = 0 hours | Racemic | Racemic | Racemic | Racemic |
| t = 6 hours | ee = 48% | ee => 98% | Racemic | Racemic |
| t = 26 hours | ee => 98% | ee => 98% | Racemic | Racemic |

This resolution was further confirmed at the 23-Liter scale while repeating an earlier run that achieved a final EE of 93%. An excellent EE of 98% for the desirable 1S,2R-indandiol was obtained with this batch as well and demonstrated reproducibility of the process.

EXAMPLE 4

LARGE SCALE PROTOCOL FOR F1 FERMENTATION

A. Seed train

The organism used was Pseudomonas putida F1 (wild type). A single-stage seed train was employed. The seed medium comprised 30 g/l trypticase soy broth and no pH adjustment was necessary. A frozen vial of the culture was thawed at room temperature, and a 0.5 ml aliquot used to inoculate 500 ml of seed medium in a 2.8 liter flask. The seed was incubated for 8 hours at 30° C. and 220 rpm on a rotary shaker with a 2" throw. Two flasks were then combined (giving a total seed volume of 1 liter) and used to inoculate the production fermentor.

B. Production stage

For each of the four runs, deionized water was added to three 200-gallon fermentors to a working volume of 630 liters. Medium ingredients (see Table 6) were charged directly to each vessel. The pH was adjusted using sulfuric acid or sodium hydroxide to 7.0. The medium was sterilized at 121°–123° C. for 35 minutes.

TABLE 6

The production medium comprised the following (per liter):

| Component | Concentration |
|---|---|
| Disodium phosphate | 10.5 g |
| Monopotassium phosphate | 5.5 g |
| Arginine | 4.0 g |
| Ammonium sulfate | 2.0 g |

TABLE 6-continued

The production medium comprised the following (per liter):

| Component | Concentration |
|---|---|
| Magnesium sulfate heptahydrate | 0.6 g |
| $CaCl_2.2H_2O$ | 130 mg |
| $ZnSO_4.7H_2O$ | 22 mg |
| $FeSO_4.7H_2O$ | 14 mg |
| EDTA | 5 mg |
| $MnSO_4.H_2O$ | 3 mg |
| $CuSO_4.5H_2O$ | 0.8 mg |
| $CoCl_2.6H_2O$ | 0.5 mg |
| $(NH_4)_2MoO_4.4H_2O$ | 0.36 mg |
| $Na_2B_4O_7.10H_2O$ | 0.35 mg |
| antifoaming agent | 1 ml |
| Silicone oil | 100 g |

C. Fermentation conditions

The fermentation was initially operated at 30° C. with a back-pressure of 0.5 bar, air flow of 100 slpm, and agitator speed of 100 rpm. The back-pressure, air flow, and agitator speed were automatically increased during the fermentation to maintain the dissolved oxygen tension at or above 50% of the value for medium saturated with air at atmospheric pressure. The pH was controlled between 6.8 and 7.4 using 25% sulfuric acid and 50% sodium hydroxide solutions.

D. Induction and bioconversion

At an age of 4–8 hours, a solution comprising 3.25 kg toluene and 1.63 kg indene in 20 liters of silicone oil was added to the fermentation medium using a Chemap needle, viton tubing, and a peristaltic pump.

E. Harvest

The oxygen utilization rate (OUR) of each fermentation batch was monitored. After about 24 hours, the OUR decreased to less than 1 mmol/l/h. The batch was harvested 6–10 hours after the drop in OUR. During this period, degradation of the unwanted isomer occurred (causing an increase in the stereoisomeric excess from about 60% to >97%). Average titer per batch was 330 mg/l.

EXAMPLE 5

Protocol For F1 Fermentation Products of Previous Example

I. ISOLATION

A. Silicone Oil Removal via Gravity Settling

Fermentation broth was harvested into a 1500 gallon stainless steel vessel. Whole broth was settled overnight. The lower aqueous layer containing product and fermentation cells was cut to two 200-gallon tanks. The waste silicone oil layer and the interface was drummed into 55-gal drums for disposal.

B. Expanded Bed Adsorption

A glass column (12 inch diameter×96 inch length) containing ~85 liters of brominated styrene divinyl benzene resin was prepared. Aqueous broth was fed via the bottom inlet of the column at 1.5–2.5 gpm. The spent broth effluent was removed out the top of the column and collected into 55 gal drums. If no product was detected by HPLC assay in the spent feed, it was pumped to the chemical sewer. If product was detected in the spent feed the drum contents were held and readsorbed to the resin at the beginning of the next batch. After all the aqueous broth was fed to the column, the column was upwashed with DI water to remove the residual broth liquid and solids from the column. The water wash was followed by a 100 gallon 95% water/5% acetonitrile upwash. Aqueous acetonitrile and water washes were collected in 55-gal drums. Any product in the aqueous acetonitrile and water washes was readsorbed to the resin at the beginning of the next batch. Flow was stopped and resin allowed to resettle. Liquid above the resin was removed out the top of the column using a pump. The product was then eluted using 100 gallons of 20% acetonitrile/80% water and eluate was collected in 5 gallon jugs. The resin was regenerated by washing with 50 gallons of acetonitrile and then re-equilibrated by washing with several bed volumes of DI water.

C. Rich Cut Concentration/Isopropyl Acetate Extraction

Products richcuts were vacuum concentrated in a 50-gallon glass-lined reactor. Liquid level was maintained at maximum working volume by continuously feeding richcuts until all richcuts were charged. Then volume was concentrated to a final volume of 25 gallons. This procedure helped minimize foaming and acetonitrile in the aqueous concentrate. An equal volume of isopropyl acetate was added to the aqueous layer via residual vacuum. Contents were agitated for 5 minutes and liquid phases were separated by gravity settling for at least 1 hour. The lower aqueous raffinate phase was cut to 55-gal drum and the upper organic extract was also cut to a 55-gal drum. Any emulsion layer was always cut forward with the aqueous layer. The aqueous layer was recharged to the 50-gallon reactor and re-extracted three more times with equal volumes of isopropyl acetate to recover >95% of the product in the combined richcuts. Lean extracts (3 & 4) were held and used for initial extraction of the next batch to reduce solvent usage.

D. IPAc Concentration/Crystallization

The isopropyl acetate extracts were partially vacuum concentrated to a volume of 7–10 gallons in a 50-gallon glass-lined reactor. The concentrate was transferred to 5 gallon jugs. The concentrate was then charged to the 20-liter rotovap via a medium porosity line filter which removed some brown particulate matter. The extracts were further concentrated to about 200 grams cis-indandiol/liter. The cis-indandiol began to crystallize during the final concentration and the crystallization was completed by cooling to 5°–10° C. and aging overnight. The crystals were vacuum filtered on a sintered glass filter and washed with cold (5° C.) isopropyl acetate, isopropyl acetate/hexane (1:1), and hexane. Crystals were dried under vacuum with no heat.

EXAMPLE 6

PROTOCOL FOR 421-5

Seed Development

A 2 liter non-baffled shake flask with 300 ml of seed medium was used to prepare the seed culture for the 23 liter production vessel. The seed medium consisted of 3% tryptic soy broth (TSB). The seed medium was sterilized in situ by autoclaving it for 20 minutes. A frozen vial containing the 421-5 culture was thawed and 300 µl of the thawed culture was asceptically transferred to the seed flask after the flask has been cooled to room temperature. The flask was then incubated at 30° C. on a shaker at 200–250 RPM for 14 hours and the entire contents of the seed flask were used to inoculate the 23 liter tank.

Fermentation/Bioconversion (23 liter scale)

A chemically defined medium described in Table 8 was batched in the 23 liter production vessel with a 15 liter working volume. The process variables in the fermentation are described in Table 7.

TABLE 7

| Process Variable | Initial Set Point | Other Conditions |
|---|---|---|
| Temperature | 30° C. | Controlled throughout |
| pH | 7.20 | Controlled throughout |

TABLE 7-continued

| Process Variable | Initial Set Point | Other Conditions |
| --- | --- | --- |
| Back Pressure | 0.34 bar | Controlled throughout |
| Agitation | 450 | Varied to control DO above 50% |
| Air Flow | 7.5 lpm | Varied to control DO above 45% |
| Dissolved Oxygen | 100% | Controlled above 45% usin agitation and airflow |

The 23 liter fermentor was batched with all salts and soybean oil and sterilized in place for 1 hour. Glucose was sterilized separately and was added to the batch as a shot in the beginning. The batch was inoculated with the entire 300 ml seed and was cultivated for up to 28 hours using the process variable values shown in Table 7.

TABLE 8

Semi-defined medium composition for *P. putida* 421–5 fermentation

| Component | Concentration |
| --- | --- |
| 1. Glucose # | 20 mM |
| 2. $(NH_4)_2SO_4$ | 10 g/l |
| 3. $K_2HPO_4$ | 6 g/l |
| 4. $FeSO_4.7H_2O$ | 0.03 g/l |
| 5. $MgSO_4.7H_2O$ | 1.2 g/l |
| 6. EDTA* | 0.0167 g/l |
| 7. Soybean Oil | 20% (v/v) |
| 8. A-9 Solution | 90 ml |

Initial concentration. Glucose fed at controlled rate thereafter.
*Added only when glucose used.

Indene (reagent grade, 99+%) was batched at 2.5 g/L initially and was supplemented in a shot wise manner after 10 hours at 0.3 g/L every hour for the next 10 hours and 0.6 g/l every 2 hours for the next 8 hours. The pH was controlled at 7.2 initially with NaOH and later (approx. 10 hours) with $NH_4OH$ to avoid nitrogen starvation. Glucose was fed continuously at 4 g/L/hr after 6 hours of fermentation time. The feed was stopped after 6–8 hours of continuous feeding. Dissolved oxygen was controlled above 45% for the entire duration of the batch using agitation and air flow in a cascade mode. The air flow control kicked in after the maximum agitation rate of 750 RPM was reached. Using this protocol, a peak indandiol titer of 2 g/L (80% EE) was reached after 20 hours of fermentation.

EXAMPLE 7
Isolation of Toluene Dioxygenase Mutants

A. Cultivation Methods

*Pseudomonas putida* F1 (DSM 6899) and mutants thereof were grown and maintained using tryptic soy agar (TSA) and tryptic soy broth (TSB). All cultures were incubated at 30° C. Plate cultures were stored at 4° C. for 2 to 4 weeks and were used as a source of inoculum for conversion experiments. Liquid cultures were diluted 1:1 with 20% (v/v) glycerol and stored as aliquots at –70° C. Solid culture medium was prepared by supplementing medium formulations with 20 gm/l agar. To grow solid medium cultures in the presence of toluene vapors, 100×15 mm glass petri dishes containing the solid medium of choice were placed in a glass dessicator along with 3 to 5 ml of toluene in a 15 ml glass test tube and incubated at the appropriate temperature.

B. Conversion of Indene to cis-1S,2R-indandiol-Shake-Flask Scale

A minimal salts medium with citrate (MMC) or without carbon source (MM) was used for the conversion of indene to cis-1S,2R-indandiol and consisted of (in gm/l): 3-[N-Morpholino]-propanesulfonic acid (MOPS), 20.9; sodium citrate $2H_2O$, 2.94; $K_2HPO_4$, 2; $(NH_4)_2SO_4$, 1; $MgSO_4 7H_2O$, 0.4; $FeSO_4 7H_2O$, 0.010; A9 solution, 2.5 ml; pH, 7.2. The A9 solution consisted of (in mg/l): $H_3BO_3$, 300; $ZnCl_2$, 50; $MnCl_2 4H_2O$, 30; $CoCl_2$, 200; $CuCl_2 2H_2O$, 10; $NiCl_2 6H_2O$, 20; and $NaMoO_4 2H_2O$, 30. Solid culture medium was prepared by supplementing the above formula with 20 gm/l agar. Twenty milliliters of minimal salts medium plus 5 ml of soybean oil or silicone oil were sterilized in a 250 ml 3-baffled Erlenmeyer flask. After sterilization and cooling, indene or toluene were added to flasks where required.

When washed cells were employed for conversion experiments, 25 ml, overnight cultures were grown in TSB followed by centrifugation and resuspension in 20 ml of MM medium. The cell suspension was transferred to a 250 ml 3-baffled Erlenmeyer flask along with 2.5 ml of silicone oil and 1 gm/l indene (based on entire culture volume). The cultures were incubated at 30° C. with 180 RPM rotary agitation for 24 hours after which time an aliquot of the culture supernatant (aqueous) was analyzed for the cis-1S,2R-indandiol concentration by reverse-phase HPLC.

Alternatively, the conversion of indene to cis-1S,2R-indandiol was carried out by actively metabolizing cells in shake-flask cultures. A 250 ml 3-baffled Erlenmeyer flask containing 20 ml of MMC medium, 5 ml of soybean oil, and 2.5 gm/l indene (based on entire culture colume) was inoculated with 0.2 ml from an overnight TSB culture. Production flasks were incubated as above and individual flasks were extracted appropriately to determine cis-1S,2R-indandiol titers and stereoisomeric purity. For time course experiments, several flasks for each culture were inoculated and entire flasks were extracted at each time point to determine cis-1S,2R-indandiol titer and stereoisomeric purity.

C. Methods for Isolating Toluene-independent Cultures

Two mutation and screening procedures were employed to generate mutants of *P. putida* F1 capable of converting indene to cis-1S,2R-indandiol without requiring toluene in the culture medium. Central to both screening procedures is the ability of many aromatic-hydrocarbon utilizing microbes to convert indole to indigo (blue pigment) (Ensley, et al., Science 222, 167 (1983); Clarke, P. H., et al., FEMS Microbiol. Lett., 24, 109 (1984)). Toluene dioxygenase converts indole to cis-indole 2,3 dihydrodiol (Clarke, et al., 1984). Spontaneous elimination of water forms indoxyl followed by air oxidation producing indigo (Ensley, et al., supra 1983).

Colonies of *P. putida* F1 incubated in the presence of toluene vapors, become dark blue within 18 to 24 hours while colonies incubated in a normal air atmosphere (with a noninducing carbon source in the medium) require up to 36 hours to attain a blue color. Thus the indole to indigo conversion serves as a useful biochemical marker for dioxygenase activity and can be used to detect dioxygenase activity in the absence of toluene.

In procedure 1, cells were grown overnight in TSB at 30° C. and diluted $10^{-4}$ with phosphate buffer (100 mM, pH 7.2). Several 18×150 mm test tubes containing 3 ml of MMC medium plus 0 (control), 10, 20, 30, 40, 50, 75, or 100 mg/l ICR 191 were inoculated with 0.1 ml of the diluted inoculum. Test tube cultures were incubated in the dark at 30° C. with 220 RPM agitation. After a 16 to 18 hour incubation, the 30 mg/l ICR 191 culture displayed a trace of growth while the 20 mg/l ICR 191 culture had a level of growth that was approximately half that of the control. ICR 191 concentrations above 30 mg/l completely inhibited growth while the 10 mg/l concentration had no detectable effect on growth. The cells from 20 mg/l ICR 191 culture were harvested by centrifugation, washed twice with phosphate buffer.

D. Isolation of mutant 421-5

After performing a viable cell count on the selected tube, 1 ml of an appropriate dilution (so that no colony confluence was observed) was plated on Petri dishes (24.5 cm×24.5 cm) containing modified mineral medium (0.040 g/L FeSO$_4$) with 1 mM indole as indicator for dioxygenase activity. After about 36 hours of incubation, at 30° C., several plates showed the presence of a few dark blue colonies. A total of 16 colonies were sterily picked off the plate and replated on a similar medium. After another 36 hours of incubation, each of these isolates were inoculated to tubes containing 5 ml of tryptic soy broth. After an incubation of 18 hours at 30° C., 1 ml of sterile silicone oil and 5 μl of indene were added to each tube. The tubes were returned to the same incubation conditions for an additional 24 hours. After centrifugation, the supernatant was assayed for the presence of indandiol, employing a reverse phase HPLC. Under these non-induced conditions, isolate 421-5 was found to produce about 426 mg/L of indene, versus 100 mg/L for the parent culture. We examined about 200,000 colonies before we isolated the mutant 421-5 (a.k.a. MB 5652).

For procedure 2, an aliquot of a TSB overnight culture was harvested by centrifugation and washed twice with citrate buffer (100 mM, pH 5.5). N-Methyl-N'-nitro-N-nitrosoguanidine (NTG) was added to a final concentration of 50 mg/l and incubated at room temperature with occasional mixing. After a 30 minute incubation, cells were washed twice with phosphate buffer and diluted appropriately.

Aliquots of the mutated population (0.1 ml) were spread on solid indole indicator medium in 100×15 mm glass petri dishes and incubated at 30° C. in the presence of toluene. White colonies (no indigo production, dioxygenase and toluene negative) were picked over to TSA. Single dioxygenase-negative colonies were inoculated into 250 ml 3-baffled Erlenmeyer glasks containing minimal medium with silicone oil as the second phase and no citrate. Toluene was introduced to the culture in the silicone oil phase at final overall concentration of 5 gm/l. Within 48 to 72 hours of incubation at 30° C. with 180 RPM rotary shaking, spontaneous, toluene-positive revertants began to grow out. Colonies from these revertant cultures were isolated and evaluated for toluene-independent conversion of indene to cis-1S,2R-indandiol in the shake flask fermentation process. One such culture isolated in this fashion was 419-11R3.

EXAMPLE 8

A. Conversion of Cis-1S,2R-Indandiol to Cis-1S-Amino-2R-Indanol

Experimental

| Materials | Amount | MW | Moles |
|---|---|---|---|
| Cis-1S,2R-indandiol | 100 g | 150.18 | 0.66 |
| 20% oleum sulfuric acid/sulfur trioxide | 66.2 mL | 98.08 | 1.33 |
| Acetonitrile | 633.3 mL | | |
| Water | 1000 mL | | |

Cis-1S,2R-Indandiol (100 g, 0.66 mole) was added to acetonitrile (633 mL) at 25° C. then cooled to −25° to −30° C. A solution of 20% oleum (66.2 mL, 1.33 mole) was added, while maintaining the temperature below −10° C. After the addition was completed, the mixture was warmed to 20° C., aged for 1.5 h, then water was added (1000 mL). The acetonitrile solvent was distilled until the internal temperature reached approximately 100° C. The mixture was aged at this temperature for 4.5 h. The solution was concentrated to 100 g of amino-indanol/L. Yield of 86.7%, at >99% ee.

B. Isolation of (−) Cis-Aminoindanol Using Reverse Ion Pairing Extractive Workup of the Ritter Solution Starting From Diol

| Materials | Amount | MW | Moles |
|---|---|---|---|
| Step A Product | 548.7 g (50.0 g cis-aminoindanol | 149.2 | 0.335 |
| 1-butanol | 501 mL | | |
| 50% NaOH | 145 mL | 40 | |
| Water | 625 mL | | |
| L-tartaric acid | 60.0 g | 150.1 | 0.4 |

Into a 2 liter round-bottom flask equipped with a thermometer and over-head stirrer was placed 548.7 g of solution from the Ritter (50.0 g cis-aminoindanol from Step A) and 167 mL of 1-butanol. The addition of 50% NaOH was started while maintaining temperature below 40° C. with a water bath. This addition was continued until the pH was greater than 12. A total of 103 mL of 50% NaOH was added. The mixture darkened during the addition.

The mixture was placed in a separatory funnel, and the layers separated. The aqueous layer was then extracted with 2×167 mL 1-butanol. The three organic layers were combined and extracted with a solution of 60.0 g L-tartaric acid (1.2 mole equivalents) in 250 mL of water. The layers were separated and the organic layer was further extracted with 3×125 mL of water. The combined aqueous layer was then concentrated under vacuum to 220 mL. Some solids had begun to precipitate.

The concentrate was rinsed into a 500 mL round-bottom flask equipped with a thermometer and over-head stirrer with 30 mL of water. The addition of 50% NaOH was started. During the addition, the temperature was maintained below 45° C. with a water batch. The cis-aminoindanol started to crystallize between pH 8 and 9. The addition was continued until the pH was greater than 12. A total of 42 mL of 50% NaOH was added. The mixture was slowly cooled to 0°–5° C., and aged for 2 hours, filtered (the filtration was slow) and washed with 150 mL of 0°–5° C. water. Dry in a vacuum oven with a nitrogen purge at 45° C. for 18 hours. Yield of (−)cis-aminoindanol:45.74 g (96.6 wt %); 2.1% trans-aminoindanol.

C. Isolation of (−)-Cis-Aminoindanol Using A Dowex 50×8 Resin Column Workup of the Ritter Solution Starting From Diol Experimental

| Materials | Amount | MW | Moles |
|---|---|---|---|
| Step A Product | 550 mL (50.0 g cis-aminoindanol | 149.2 | 0.335 |
| Dowex 50x8 (100 mesh) resin | 500 mL (in water) | | |
| 50% NaOH | 34.5 g | 40 | |
| Water | 600 | | |
| 20% MeCN in water | 2175 | | |

A 500 mL Dowex 50×8 (100 mesh) resin column was set up. The column was washed, then back washed with water.

The diol Ritter solution (50.0 g cis-aminoindanol in 550 mL Product of Step A) was loaded onto the column with a flow rate of 1.5 bed volumes per hour. The column was then washed with 600 mL of water. There was less than 1 % breakthrough.

At first, the elution was tried using NaCl but this was not efficient. A total of 12.3 g of cis-aminoindanol was recovered. The column was washed with 500 mL of 20% MeCN in water followed by the elution with NaOH below.

Dissolve 20.3 g of 50% NaOH in 250 mL of 20% MeCN in water. Pump the solution up flow onto the column. Follow with a 100 mL 20% MeCN line rinse. Let stand for 1.75 hours. Start eluting the column with a 1.5–2 bed volume flow rate. When the solvent reaches the resin bed, elute with 750 mL of 20% MeCN in water. The total cis-aminoindanol eluted was 16.7 g.

Dissolve 11.5 g of 50% NaOH in 250 mL of 20% MeCN in water. Pump the solution up flow onto the column. Follow with a 100 mL 20% MeCN line rinse. Let stand for 1.75 hours. Start eluting the column with a 1.5–2 bed volume flow rate. When the solvent reaches the resin bed, elute with 750 mL of 20% MeCN in water. The total cis-aminoindanol eluted with 16.7 g.

Dissolve 2.7 g of 50% NaOH in 250 mL of 20% MeCN in water. Pump the solution onto the column. Start eluting the column with a 1.5–2 bed volume flow rate. When the solvent reaches the resin bed, elute with 500 mL of 20% MeCN in water. The total cis-aminoindanol eluted was 3.0 g.

The pH of the combined eluents from the first two elutions was adjusted to 2.95 with concentrated HCl. The solution was then concentrated to 228 mL under vacuum. This solution was then used in various crystallization experiments.

The total recovery of cis-aminoindanol from the NaCl and NaOH elutions was 48.7 g.

EXAMPLE 9
Preparation of Amide 9

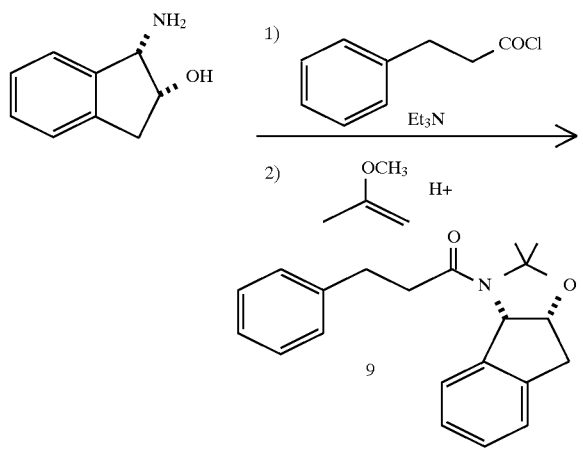

A solution of (−)-cis-1-aminoindan-2-ol (884 g, 5.93 mol) in 17.8 L of dry THF (KF=55 mg/mL) (KF stands for Karl Fisher titration for water) and triethylamine (868 mL, 6.22 mol) in a 50 L round bottom flask equipped with a thermocouple probe, mechanical stirrer, and a nitrogen inlet adapter and bubbler, was cooled to 15° C. Then, 3-phenylpropionyl chloride (1000 g, 5.93 mol) was added over 75 minutes, while the internal temperature between 14°–24° C. with an ice-water cooling batch. After addition, the mixture was aged at 18° to 20° C. for 30 minutes and checked by HPLC analysis for the disappearance of (−)-cis-1-aminoindan-2-ol.

Progress of the reaction is monitored by high performance liquid chromatography (HPLC) analysis: 25 cm Dupont C8-RX column, 60:40 acetonitrile/10 mM ($KH_2PO_4$/$K_2HPO_4$), 1.0 mL/min., injection volume=20 mL, detection=200 nm, sample preparation=500×dilution. Approximate retention times:

retention time (min) identity
6.3 cis-aminoindanol

The reaction was treated with pyridinium p-toluenesulfonate (241 g, 0.96 mol, 0.16 equiv.) and stirred for 10 minutes (the pH of the mixture after diluting 1 mL sample with an equal volume of water is between 4.3–4.6). Then, 2-methoxypropene (1.27 L, 13.24 mol, 2.2 equiv.) was added and reaction was heated to 38°–40° C. for 2 h. The reaction mixture was cooled to 20° C. and partitioned with ethyl acetate (12 L) and 5% aqueous $NaHCO_3$ (10 L). The mixture was agitated and the layers were separated. The ethyl acetate extract was washed with 5% aqueous $NaHCO_3$ (10 L) and water (4 L). The ethyl acetate extract was dried by atmospheric distillation and solvent switched to cyclohexane (total volume of ~30 L). At the end of the distillation and concentration (20 volume % of ethyl acetate extraction volume), the hot cyclohexane solution was allowed to slowly cool to 25° C. to crystallize the product. The resulting slurry was further cooled to 10° C. and aged for 1 h. The product was isolated by filtration and the wet cake was washed with cold (10° C.) cyclohexane (2×800 mL). The washed cake was dried under vacuum (26" of Hg) at 40° C. to afford 1.65 kg of acetonide 9 (86.4%, 98 area % by HPLC). $^1$H NMR (300.13 MHz, $CDCl_3$, major rotamer) δ7.36–7.14 (m, 9H), 5.03 (d, J=4.4, 1H), 4.66 (m, 1H), 3.15 (m, 2H), 3.06 (br s, 2H), 2.97 (m, 2H), 1.62 (s, 3H), 1.37 (s, 3H); $^{13}$C NMR (75.5 MHz, $CDCl_3$, major rotamer) $δ_c$ 168.8, 140.9, 140.8, 140.6, 128.6, 128.5, 128.4, 127.1, 126.3, 125.8, 124.1, 96.5, 78.6, 65.9, 38.4, 36.2, 31.9, 26.5, 24.1.

Analysis calculated for $C_{21}H_{23}NO_2$: C, 78.47; H, 7.21; N, 4.36. Found: C, 78.65; H, 7.24; N, 4.40.

EXAMPLE 10
Preparation of Epoxide 11 Tosylate Method

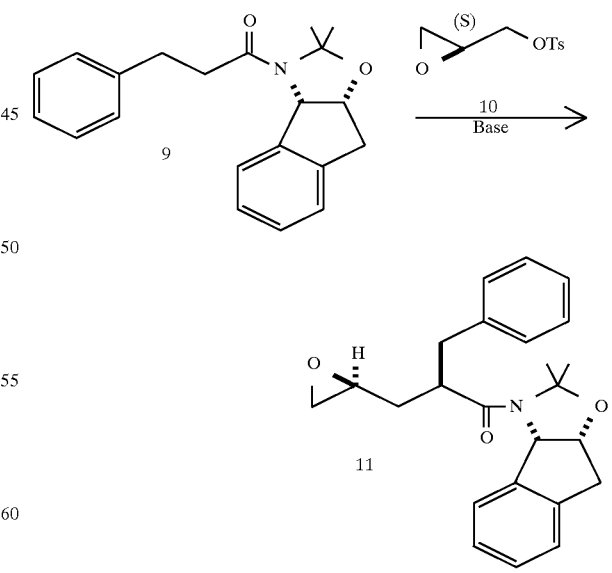

A solution of acetonide 9 (1 000 g, 3.11 mol) and 2(S)-glycidyl tosylate 10 (853 g, 3.74 mol, 1.2 equiv.) in 15.6 L of THF (KF=22 mg/mL) in a 50 L 4-neck round bottom flask, equipped with a thermocouple, mechanical stirrer, addition funnel and nitrogen inlet adapter was degassed 3 times via vacuum-nitrogen purge and cooled to −56° C. Then, lithium hexamethyldisilazide (LiN[(CH$_3$)$_3$Si]$_2$)(2.6 L, 1.38M, 1.15 equiv.) was added over 2 h, while keeping the internal temperature between −50° to −45° C. The reaction mixture was stirred at −45° to −40° C. for 1 h and then allowed to warm to −25° C. over 1 h. The mixture is stirred between −25° to −22° C. for 4 h (or until the starting acetonide is 3.0 area %).

Progress of the reaction is monitored by HPLC analysis: 25 cm×4.6 nm Zorbax Silica column, 20% ethyl acetate in hexane, 2.0 mL/min, injection volume=20 mL, detection =254 nm, sample preparation=100×dilution. Approximate retention times:

| retention time (min) | identity |
|---|---|
| 5.5 | amide 9 |
| 6.5 | glycidyl tosylate 10 |
| 13.5 | epoxide 11 |

The reaction mixture was quenched with DI water (6.7 L) at −15° C. and partitioned with ethyl acetate (10 L). The mixture was agitated and the layers were separated. The ethyl acetate extract was washed with a mixture of 1 % aqueous NaHCO$_3$ (5 L) and saturated NaCl (0.5 L). The ethyl acetate extract (28.3 L) was concentrated by vacuum distillation (28" of Hg) and additional ethyl acetate was added to complete the solvent switch to ethyl acetate (final volume=11.7 L). The ethyl acetate concentrate was further solvent switched to MeOH to crystallize the product and concentrated to a final volume of 3.2 L. The residual ethyl acetate solvent was removed by charging 10 L of methanol and collecting 10 L of distillate. The resulting slurry was stirred at 22° C. for 1 h, then cooled to 5° C. and aged for 0.5 h. The product was isolated by filtration and the wet cake was washed with cold methanol (2×250 mL). The washed cake was dried under vacuum (26" of Hg) at 25° C. to afford 727 g of epoxide 11 (61.2%, 98.7 area % of the major epoxide by HPLC). $^{13}$C NMR (300 MHz, CDCl$_3$) δ171.1, 140.6, 140.5, 139.6, 129.6, 128.8, 128.2, 127.2, 126.8, 125.6, 124.1, 96.8, 79.2, 65.8, 50.0, 48.0, 44.8, 39.2, 37.4, 36.2, 26.6, 24.1.

EXAMPLE 11

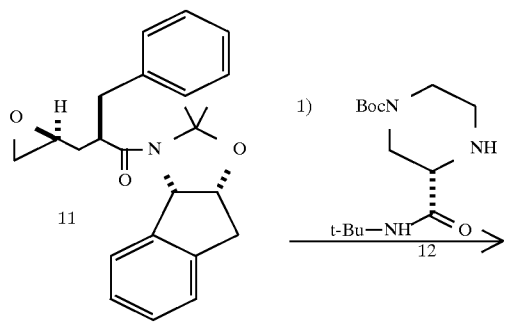

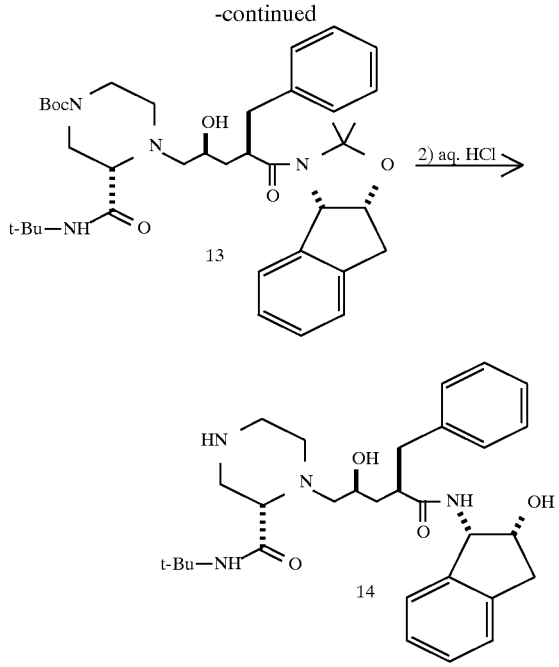

A slurry of the 2(S)-t-butylcarboxamide-4-N-Boc-piperazine 12 (1950 g, 6.83 mol, >99.5% ee) (ee= stereoisomeric excess) and the epoxide 11 (2456 g, 97.5:2.5 mixture of 4S/R epoxides, 6.51 mol) in isopropanol (2-propanol, 18.6 L) in a 72 L round bottom flask with four inlets, equipped with a mechanical stirrer, reflux condenser, steam bath, Teflon coated thermocouple and nitrogen inlet, was heated to reflux (internal temperature was 84°–85° C.). After 40 min, a homogeneous solution was obtained. The mixture was heated at reflux for 28 h.

The internal temperature during reflux was 84°–85° C. Progress of the reaction was monitored by HPLC analysis: 25 cm Dupont C8-RX column, 60:40 acetonitrile/10 mM (KH$_2$PO$_4$/K$_2$HPO$_4$), 1.0 mL/min., detection=220 nm, sample preparation=2 μL, reaction mixture diluted to 1 mL in acetonitrile. Approximate retention times:

| retention time (min) | identity |
|---|---|
| 4.8 | piperazine 12 |
| 8.9 | epoxide 11 |
| 15.2 | coupled product 13 |

After 28 h, the remaining epoxide 11 and coupled product 13 (by HPLC analysis) were 1.5 area % and 91–93 area %, respectively. The mixture was cooled to 0° to 5° C. and 20.9 L of 6N HCl was added while keeping the temperature below 15° C. After the addition was complete, the mixture was warmed to 22° C. Evolution of gas is noted at this point (isobutylene). The mixture was aged at 20° to 22° C. for 6 h.

Progress of the reaction was monitored by HPLC analysis: same conditions as above. Approximate retention times:

| retention time (min) | identity |
|---|---|
| 7.0 | cis-aminoindanol |
| 11.9 | penultimate 14 |
| 15.1 | coupled product 13 |

The mixture was cooled to 0° C and 7.5 L of 50% NaOH was slowly added to adjust the pH of the mixture to pH=11.6, while keeping the temperature less than 25° C. during the addition. The mixture was partitioned with ethyl acetate (40 L) and water (3 L). The mixture was agitated and the layers were separated. The organic phase (60 L) was concentrated under reduced pressure (29" of Hg) and solvent switched to DMF and concentrated to a final volume of 10.5 L (KF=1.8 mg/mL). The HPLC assay yield of 14 in ethyl acetate was 86.5%. The penultimate compound 14 in DMF was directly used in the next step without further purification. For isolated 14: $^{13}$C NMR (75.4 MHz, CDCl$_3$) δ175.2, 170.5, 140.8, 140.5, 139.9, 129.1, 128.5, 127.9, 126.8, 126.5, 125.2, 124.2, 73.0, 66.0, 64.8, 62.2, 57.5, 49.5, 47.9, 46.4, 45.3, 39.6, 39.3, 38.2, 28.9.

EXAMPLE 12
Preparation of monohydrate of Compound J

| Retention time (min) | Identity |
|---|---|
| 2.7 | DMF |
| 4.2 | 3-picolyl chloride |
| 4.8 | Compound J |
| 9.1 | penultimate 14 |

The mixture was aged at 68° C. until the residual penultimate compound 14 was <0.3 area % by HPLC analysis.

The mixture was stirred at 68° C. for 4 h, then cooled to 25° C. and partitioned with ethyl acetate (80 L) and a mixture of 24 L of saturated aqueous NaHCO$_3$ and distilled water (14 L). The mixture was agitated at 55° C. and the layers were separated. The ethyl acetate layer was washed three times with water (20 L) at 55° C. The washed ethyl acetate layer is concentrated at atmospheric pressure to a final pot volume of 30 L. At the end of the atmospheric concentration, water (560 mL) was added to the hot solution and the mixture was cooled to 55° C. and seeded with Compound J monohydrate. The mixture was cooled to 4° C. and filtered to collect the product. The product was washed with cold ethyl acetate (2×3 L), and dried at house vacuum at 25° C. to afford 2905 g (70.7%) of Compound J monohydrate as a white solid.

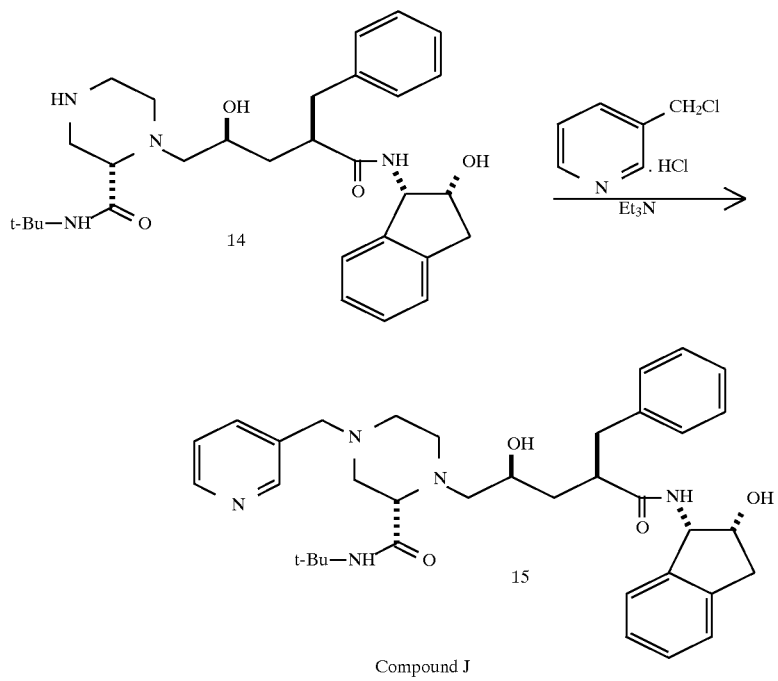

Compound J

The solution of 14 in DMF (10.5 L, KF=10 mg/mL) from the previous step was charged with 8 L of sieve dried DMF (KF. <30 mg/L) and the mixture was heated with a steam bath under vacuum of 30" of Hg to distill off mainly water and/or any residual isopropanol or ethyl acetate solvent. The final concentrate volume was 13.5 L (KF=1.8 mg/mL) and then triethylamine (2.86 L, 20.51 mol) was added to the 25° C. solution followed by 3-picolyl chloride hydrochloride (96%, 1287 g, 7.84 mol). The resulting slurry was heated to 68° C.

The progress of the reaction was followed by HPLC analysis using the same conditions as the previous step. Approximate retention times:

EXAMPLE 13

Pyrazine-2-tert-butyl carboxamide 17

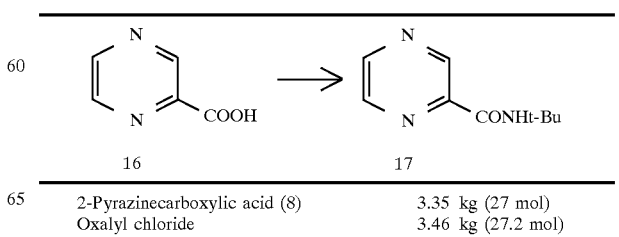

| 2-Pyrazinecarboxylic acid (8) | 3.35 kg (27 mol) |
|---|---|
| Oxalyl chloride | 3.46 kg (27.2 mol) |

-continued

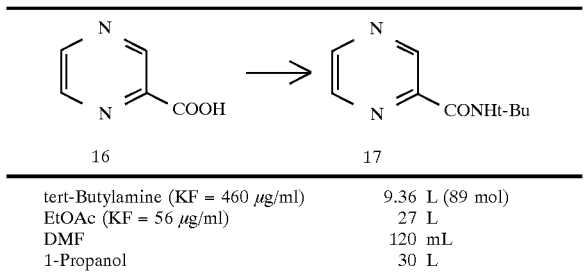

| tert-Butylamine (KF = 460 μg/ml) | 9.36 L (89 mol) |
| EtOAc (KF = 56 μg/ml) | 27 L |
| DMF | 120 mL |
| 1-Propanol | 30 L |

The carboxylic acid 16 was suspended in 27 L of EtOAc and 120 mL of DMF in a 72 L 3-neck flask with mechanical stirring under $N_2$ and the suspension was cooled to 2° C. The oxalyl chloride was added, maintaining the temperature between 5° and 8° C.

The addition was completed in 5 h. During the exothermic addition CO and $CO_2$ were evolved. The HCl that was formed remained largely in solution. A precipitate was present which is probably the HCL salt of the pyrazine acid chloride. Assay of the acid chloride formation was carried out by quenching an anhydrous sample of the reaction with t-butylamine. At completion <0.7% of acid 16 remained.

The assay for completion of the acid chloride formation is important because incomplete reaction leads to formation of a bis-tert-butyl oxamide impurity.

The reaction can be monitored by HPLC: 25 cm Dupont Zorbax RXC8 column with 1 mL/min flow and detection at 250 nm; linear gradient from 98% of 0.1% aqueous $H_3PO_4$ and 2% $CH_3CN$ to 50% aqueous $H_3PO_4$ and 50% $CH_3CN$ at 30 min. Retention times: acid 16=10.7 min, amide 17=28.1 min.

The reaction mixture was aged at 5° C. for 1 h. The resulting slurry was cooled to 0° C. and the tert-butylamine was added at such a rate as to keep the internal temperature below 20° C.

The addition required 6 h, as the reaction was very exothermic. A small portion of the generated tert-butylammonium hydrochloride was swept out of the reaction as a fluffy white solid.

The mixture was aged at 18° C. for an additional 30 min. The precipitated ammonium salts were removed by filtration. The filter cake was washed with 12 L of EtOAc. The combined organic phases were washed with 6 L of a 3% $NaHCO_3$ and 2×2 L of saturated aq. NaCl. The organic phase was treated with 200 g of Darco G60 carbon and filtered through Solka Flok and the cake was washed with 4 L of EtOAc.

Carbon treatment efficiently removed some purple color in the product.

The EtOAc solution of 17 was concentrated at 10 mbar to 25% of the original volume. 30 L of 1-propanol were added, and the distillation was continued until a final volume of 20 L was reached.

At this point, the EtOAc was below the limit of detection in the $^1H$ NMR (<1%). The internal temperature in this solvent change was <30° C. A 1-propanol/EtOAC solution of 3 was stable to reflux atmospheric pressure for several days.

Evaporation of an aliquot gave a tan solid m.p. 87°–88° C. $^{13}C$ NMR (75 MHz, $CDCl_3$, ppm) 161.8, 146.8, 145.0, 143.8, 142.1, 51.0, 28.5.

EXAMPLE 14 rac-2-tert-Butyl-carboxamide-piperazine 18

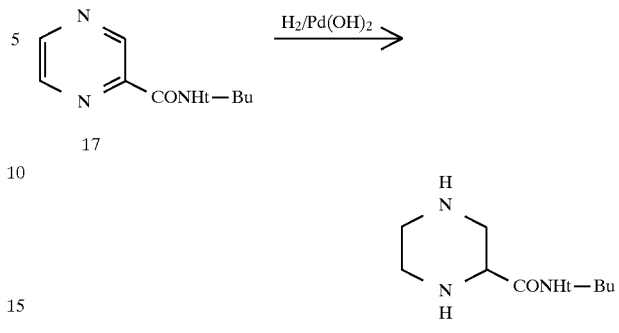

Materials

Pyrazine-2-tert-butylcarboxamide 17 2.4 kg (13.4 mol) in 1-Propanol solution 12 L 20% $Pd(OH)_2/C$ 16 wt.% water 144 g.

The pyrazine-2-tert-butylcarboxamide 17/1-propanol solution was placed into the 5 gal autoclave. The catalyst was added and the mixture was hydrogenated at 65° C. at 40 psi (3 atm) of $H_2$.

After 24 h the reaction had taken up the theoretical amount of hydrogen and GC indicated <1% of 17. The mixture was cooled, purged with $N_2$ and the catalyst was removed by filtration through Solka Floc. The catalyst was washed with 2 L of warm 1-propanol.

It was found that the use of warm 1-propanol during washing of the filter cake improved filtration and lowered the losses of product on the filter cake.

The reaction was monitored by GC: 30 m Megabore column, from 100° C. to 160° C. at 10° C./min, hold 5 min, then at 10° C./min to 250° C., retention times: 17=7.0 min, 18=9.4 min. The reaction could also be monitored by TLC with EtOAc/MeOH (50:50) as solvent and Ninhydrin as developing agent.

Evaporation of an aliquot indicated that the yield over amidation and hydrogenation is 88% and that the concentration of 18 is 133 g/L.

Evaporation of an aliquot gave 18 as a white solid m.p. 150°–151° C.; $^{13}C$ NMR (75 MHz, $D_2O$, ppm) 173.5, 59.8, 52.0, 48.7, 45.0, 44.8, 28.7.

EXAMPLE 15

(S)-2-tert-Butyl-carboxamide-piperazine bis (S)-Camphorsulfonic acid salt (S)-19

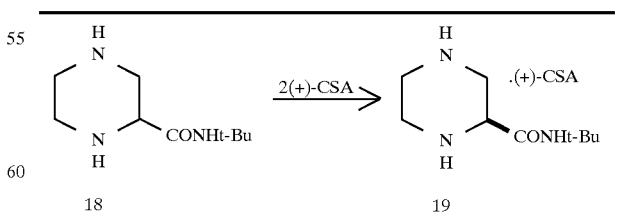

Materials

| rac-2-tert-Butyl-carboxamide-piperazine 18 | 4.10 kg (22.12 mol) |
| in 1-Propanol Solution | in 25.5 Kg solvent |
| (S)-(+)-10-Camphorsulfonic acid | 10.0 Kg (43.2 mol) |

-continued

[Scheme: Compound 18 (piperazine with CONHt-Bu) → via 2(+)-CSA → Compound 19 (piperazine·(+)-CSA salt with CONHt-Bu)]

Materials

| | |
|---|---|
| 1-Propanol | 12 L |
| Acetonitrile | 39 L |
| Water | 2.4 L |

The solution of amine 18 in 1-propanol was charged to a 100 L flask with an attached batch concentrator. The solution was concentrated at 10 mbar and a temperature <25° C. to a volume of ca 12 L.

At this point the product had precipitated from the solution, but went back into a solution when the mixture was heated to 50° C.

Analysis of a homogeneous aliquot indicated that the concentration of 18 was 341 g/L. The concentration was determined by HPLC: 25 cm Dupont Zorbax RXC8 column with 1.5 mL/min flow and detection at 210 nm, isocratic (98/2) $CH_3CN/0.1\%$ aqueous $H_3PO_4$. Retention time of 18:2.5 min.

Acetonitrile (39 L) and water (2.4 L) were added to give a clear, slightly brown solution.

Determination of the water content by KF titration and $CH_3CN/1$-propanol ratio by $^1H$ NMR integration showed that the $CH_3CN/1$-propanol/$H_2O$ ratio was 26/8/1.6. The concentration in the solution was 72.2 g/L.

The (S)-10-camphorsulfonic acid was charged over 30 min in 4 portions at 20° C. The temperature rose to 40° C. after the CSA was added. After a few minutes a thick white precipitate formed. The white slurry was heated to 76° C. to dissolve all the solids, the slightly brown solution was then allowed to cool to 21° C. over 8 h.

The product precipitated at 62° C. The product was filtered without aging at 21° C., and the filter cake was washed with 5 L of the $CH_3CN/1$-propanol/$H_2O$ 26/8/1.6 solvent mixture. It was dried at 35° C. in the vacuum oven with $N_2$ bleed to give 5.6 Kg (39%) of 19 as a white crystalline solid m.p. 288°–290° C. (with decomp.) $[\alpha]_D^{25}=18.9°$ (c=0.37, $H_2O$). $^{13}C$ NMR (75 MHz, $D_2O$, ppm) 222.0, 164.0, 59.3, 54.9, 53.3, 49.0, 48.1, 43.6, 43.5, 43.1, 40.6, 40.4, 28.5, 27.2, 25.4, 19.9, 19.8.

The ee of the material was 95% according to the following chiral HPLC assay: an aliquot of 19 (33 mg) was suspended in 4 mL of EtOH and 1 mL of $Et_3N$. $Boc_2O$ (11 mg) was added and the reaction mixture was allowed to age for 1 h. The solvent was completely removed in vacuo, and the residue was dissolved in ca. 1 mL of EtOAc and filtered through a Pasteur pipet with $SiO_2$, using EtOAc as eluent. The evaporated product fractions were redissolved in hexanes at ca. 1 mg/mL. The stereoisomers were separated on a Daicel Chiracell AS column with a hexane/IPA (97:3) solvent system at a flow rate of 1 mL/min and detection at 228 nm. Retention times: S antipode=7.4 min, R=9.7 min.

EXAMPLE 16

(S)-2-tert-Butylcarboxamide-4-tert-butoxycarbonyl-piperazine 12 from salt 19

[Scheme: Compound 19 (·2(+)-CSA salt) → via $(Boc)_2O$ → Compound 12 (Boc-protected piperazine, S configuration)]

Materials

| | |
|---|---|
| (S)-2-tert-Butyl-carboxamide-piperazine Bis (S)-(+)-CSA salt 19, 95% ee | 5.54 Kg (8.53 mol) |
| Di-tert-butyl dicarbonate | 1.86 Kg (8.53 mol) |
| $Et_3N$ | 5.95 L (42.6 mol) |
| EtOH Punctilious 200 proof | 55 L |
| EtOAc | 2 L |

To the (S)-CSA salt 19 in a 100 L 3-neck flask with an addition funnel under $N_2$ was added EtOH, followed by triethylamine at 25° C. The solid dissolved readily on the addition of the $Et_3N$. The $Boc_2O$ was dissolved in EtOAc and charged to the addition funnel. The solution of $Boc_2O$ in EtOAc was added at such a rate as to keep the temperature below 25° C. The addition took 3 h. The reaction mixture was aged for 1 h after completion of the addition of the $Boc_2O$ solution.

The reaction can be monitored by HPLC:25 cm Dupont Zorbax RXC8 column with 1 mL/min flow and detection at 228 nm, isocratic (50/50),$CH_3CN/0.1M$ $KH_2PO_4$ adjusted to pH=6.8 with NaOH. Retention time of 12=7.2 min. The chiral assay was carried out using the same system as in the previous step. The reaction could also be monitored by TLC with a 100% EtOAc as the solvent. ($R_f$=0.7)

The solution was then concentrated to ca. 10 L at an internal temperature of <20° C. in a batch-type concentrator under 10 mbar vacuum. The solvent switch was completed by slowly bleeding in 20 L of EtOAc and reconcentrating to ca 10 L. The reaction mixture was washed into an extractor with 60 L of EtOAc. The organic phase was washed with 16 L of 5% aqueous $Na_2CO_3$ solution, 2×10 L DI water and 2×6 L of saturated aqueous sodium chloride. The combined aqueous washes were back extracted with 20 L of EtOAc and the organic phase was washed with 2×3 L water and 2×4 L of saturated aqueous sodium chloride. The combined EtOAc extracts were concentrated under 10 mbar vacuum with an internal temperature of <20° C. in a 100 L batch-type concentrator to ca. 8 L. The solvent switch to cyclohexane was achieved by slowly bleeding in ca. 20 L of cyclohexane, and reconcentrating to ca. 8 L. To the slurry was added 5 L of cyclohexane and 280 mL of EtOAc and the mixture was heated to reflux, when everything went into solution. The solution was cooled and seed (10 g) was added at 58° C. The slurry was cooled to 22° C. in 4 h and the product was isolated by filtration after a 1 h age at 22° C. The filter cake was washed with 1.8 L of cyclohexane and dried in the vacuum oven at 35° C. under $N_2$ bleed to give 1.87 Kg (77%, >99.9 area % by HPLC, R-isomer below level of detection) of 12 as a slightly tan powder. $[\alpha]_D^{25}=22.0°$ (c=0.20, MeOH), m.p. 107° C.; $^{13}C$ NMR (75 MHz, $CDCl_3$, ppm) 170.1, 154.5, 79.8, 58.7, 50.6, 46.6, 43.6, 43.4, 28.6, 28.3.

EXAMPLE 17

Preparation of racemic indene oxide

Indene (95%, 122 mL) was dissolved in methanol (812 mL) and acetonitrile (348 mL), then filtered. The filtrate was diluted with 0.05M sodium dibasic phosphate (116 mL), then adjusted to pH 10.5 with 1M aqueous sodium hydroxide. Aqueous hydrogen peroxide (35%, 105 mL) was diluted with water (53 mL) and added over 3 h, while maintaining the temperature at 25° C. and the internal pH at 10.5 with 1M aqueous sodium hydroxide (120 mL total).

After 6 h, 1M aqueous sodium metabisulfite was added (26 mL), while maintaining the pH above 8.3 by addition of 1M aqueous NaOH (39 mL). Water (700 mL) was added and the mixture extracted with methylene chloride (580 mL and 300 mL). The combined organic extracts containing indene oxide (117 g) were concentrated to a volume of 600 mL.

EXAMPLE 19

Assay for Inhibition of Microbial Expressed HIV Protease

Inhibition studies of the reaction of the protease expressed in *Eschericia coli* with a peptide substrate [Val-Ser-Gln-Asn-(betanapthyl)Ala-Pro-Ile-Val, 0.5 mg/mL at the time the reaction is initiated] were in 50 mM Na acetate, pH 5.5, at 30° C. for 1 hour. Various concentrations of inhibitor in 1.0 ul DMSO were added to 25 ul of the peptide solution in water. The reaction is initiated by the addition of 15 ul of 0.33 nM protease (0.11 ng) in a solution of 0.133M Na acetate pH 5.5 and 0.1% bovine serum albumin. The reaction was quenched with 160 ul of 5% phosphoric acid. Products of the reaction were separated by HPLC (VYDAC wide pore 5 cm C-18 reverse phase, acetonitrile gradient, 0.1% phosphoric acid). The extent of inhibition of the reaction was determined from the peak heights of the products. HPLC of the products, independently synthesized, proved quantitation standards and confirmation of the product composition. Compound J gave $IC_{50}$ of about 0.6 nM.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed is:

1. A biologically pure culture of *Pseudomonas putida* 421-5, ATCC 55687.

* * * * *